United States Patent [19]

Miklas

[11] 4,150,064
[45] Apr. 17, 1979

[54] ACTIVATING ZINC FERRITE OXIDATIVE DEHYDROGENATION CATALYSTS

[75] Inventor: Edward J. Miklas, Conroe, Tex.

[73] Assignee: Petro-Tex Chemical Corporation, Houston, Tex.

[21] Appl. No.: 598,586

[22] Filed: Jul. 24, 1975

Related U.S. Application Data

[62] Division of Ser. No. 515,235, Oct. 16, 1974, Pat. No. 3,953,370.

[51] Int. Cl.² .............................................. C07C 11/12
[52] U.S. Cl. .............................. 260/680 E; 260/683.3

[58] Field of Search .................... 423/594; 260/680 E, 260/683.3

[56] References Cited

U.S. PATENT DOCUMENTS

| | | | |
|---|---|---|---|
| 3,342,890 | 9/1967 | Croce et al. | 260/680 E |
| 3,684,447 | 8/1972 | Johnston et al. | 423/594 |
| 3,843,745 | 10/1974 | Christman et al. | 260/683.3 |
| 3,856,880 | 12/1974 | Woskow et al. | 260/680 E |
| 3,925,498 | 12/1975 | Stadig | 260/683.3 |

*Primary Examiner*—Brian Hearn
*Attorney, Agent, or Firm*—Kenneth H. Johnson

[57] ABSTRACT

Zinc ferrite oxidative dehydrogenation catalyst are activated by the use of only steam.

5 Claims, No Drawings

ACTIVATING ZINC FERRITE OXIDATIVE DEHYDROGENATION CATALYSTS

This application is a division of Ser. No. 515,235 filed Oct. 16, 1974, now U.S. Pat. No. 3,953,370.

The present invention relates to a method of activating zinc ferrite oxidative dehydrogenation catalysts.

Numerous types of dehydrogenation catalysts have been disclosed in the prior art. Generally, dehydrogenation catalysts comprise a metal compound or mixture of metal compounds. Such compounds include the metal oxides, metal salts such as the halides, phosphate, sulfates, molybdates, tungstates and the like. These catalysts are generally characterized as compounds containing a metal having a polyoxidation state, i.e., a metal having at least two oxidation states in addition to the zero oxidation state.

Among the preferred catalysts of this type are those which contain iron oxygen, and at least one other metallic element. The catalysts are often termed ferrites. Preferred ferrite catalysts have a face-centered cubic form of crystalline structure. However, the spinel structure may not occur and other types of ferrite having a hexagonal crystal are also disclosed in the art. A number of such ferrite catalysts are described in the following U.S. Pat. Nos.: 3,420,911; 3,420,912; 3,428,703; 3,440,299; 3,260,767; 3,274,285; 3,284,536; 3,303,234-7; 3,320,329; 3,334,152; 3,336,408; 3,342,890; 3,404,193; 3,437,703; 3,446,869; and 3,456,030.

Zinc ferrite has been considered a very desirable catalyst material because zinc's atomic and ionic properties are such as to make zinc superior to the other metals in the ferrite structure. Actual use of zinc ferrite established that zinc ferrite catalysts do produce superior results, i.e., higher conversion and higher selectivity, in comparison to other ferrites under the same oxidative dehydrogenation conditions.

The zinc ferrites, as well as the other ferrites, are preferably activated before being brought on stream for use in oxidative dehydrogenation. It has been the general practice to use a reducing gas such as hydrogen or even an oxidizable hydrocarbon to activate the catalyts. Hydrogen has been the preferred reducing gas. It has been the case, however, that at some plant sites, there is no source of hydrogen available. Since the reducing gas is employed only during the activation of the catalysts, it may be several months between the utilizations thereof, hence, unless hydrogen is generally available in the area, it would not be economical to have a specific facility for generating it for this occasional use.

Generally, the reducing gas is employed with steam. The function of the steam has not been fully determined, however, it had appeared to serve principally as a diluent for the reducing gas.

A principal aspect of the present invention is the provision of a process or method for the activation of zinc ferrite oxidative dehydrogenation catalyst which is not bound to a source of hydrogen. Another advantage of the present invention is the discovery of a zinc ferrite activation process which does not require a so-called reducing gas, in particular, hydrogen or a hydrocarbon. Another feature of the present invention is an improved activation, that is, an improvement in the oxidative dehydrogenation process when the catalyst is activated according this invention. These and other features and advantages will become apparent from the following description of the invention.

SUMMARY OF THE INVENTION

Briefly stated, the invention can be described in one aspect as the method of activating a zinc ferrite oxidative dehydrogenation catalyst in the substantial absence of reducing gases, comprising intimately contacting said zinc ferrite with a gaseous stream consisting essentially of steam at a temperature in the range of 700° to 1300° F. for a period of time to activate said zinc ferrite. Generally, the activation will be carried out for several hours, e.g. 4 or 5 hours, however, shorter periods of time, e.g. 15 to 20 minutes may be sufficient.

Another aspect of the present invention is the process oxidative dehydrogenation carried out using the zinc ferrite catalyst activated by steam in the absence of a reducing gas.

DETAIL DESCRIPTION OF THE INVENTION

The steam is intimately contacted with the zinc ferrite in any conventional manner. A preferred method of contacting is to dispose the catalyst in a fixed bed, for example, in a fixed bed oxidative dehydrogenation apparatus and to pass the steam therethrough. Another method would be a countercurrent flow of steam through a moving bed of catalyst particles.

The mechanism or manner of operation of the steam in achieving activation of the zinc ferrite is not understood. The temperature of the steam is in the range of 700° to 1300° F. and more preferably 800° to 1200° F. Inert gases such as nitrogen may be added without detriment; however, their presence is not necessary. The steam may be conducted through a fixed catalyst bed at an LHSV of from 0.05 to 10, generally, a flow rate in the range of 0.15 to 5 is used and has proved satisfactory.

DESCRIPTION OF THE PREFERRED EMBODIMENTS

The activated zinc ferrite catalyst may be utilized in processes for the dehydrogenation of a great variety of organic compounds to obtain the corresponding unsaturated derivative thereof. Such compounds normally will contain from 2 to 20 carbon atoms, at least one

grouping and have a boiling point below about 350° C.; such compounds may contain other elements in addition to carbon and hydrogen such as oxygen, halogens, nitrogen and sulfur. Preferred are compounds having from 4 to 12 carbon atoms and especially preferred are compounds of from 4 to 6 or 8 carbon atoms. Hydrocarbons are a preferred class of organic compounds for oxidative dehydrogenation according to the present invention.

Preferably, the dehydrogenation reaction utilizing the catalyst of the present invention will employ oxygen as one of the reactants. The oxygen is employed suitably in an amount within the range of 0.2 to about 5.0 mols of oxygen per mol of organic compound to be dehydrogenated, preferably from 0.2 to 2.5 moles per mol of organic compound to be dehydrogenated. Generally, better results may be obtained if the oxygen concentration is maintained between about 0.25 and about 1.6 mols of oxygen per mol of organic compound to be dehydrogenated, such as between 0.35 and 1.2 mols of oxygen. The oxygen may be fed to the reactor as pure oxygen, as air, as oxygen-enriched air, oxygen mixed with diluents, etc. Based on the total gaseous mixture entering the reactor good results are obtained with oxygen present in an amount from about 0.5 to 25 volume percent of the total gaseous mixture, such as in an amount from about 1 to 15 volume percent of the total. The oxygen may be added directly to the reactor or it may be premixed, for example, with a diluent or steam.

The product of the oxidative dehydrogenation is a more highly unsaturated organic compound corresponding to the feed to the reaction. The term unsaturated is used in its normal chemical connotation and includes both ethylenic and acetylenic unsaturation, for example, n-butene to butadiene and vinyl acetylene or ethyl acetylene, although the preferred products are organic compounds corresponding to the feed and having a higher degree of ethylenic unsaturation.

The oxidative dehydrogenation reaction may be carried out at atmospheric pressure, super-atmospheric pressure or at sub-atmospheric pressure. The total pressure of the system will normally be about or in excess of atmospheric pressure, although sub-atmospheric pressure may also desirably be used. Generally, the total pressure will be between about 4 p.s.i.a. and about 100 or 125 p.s.i.a. Preferably, the total pressure will be less than about 75 p.s.i.a. and excellent results are obtained at about atmospheric pressure.

Frequently, the reaction mixture to the oxidative dehydrogenation reaction will contain a quantity of steam or diluent such as nitrogen with the range generally being between about 2 and 40 mols of steam per mol of organic compound to be dehydrogenated. Preferably, steam will be present in an amount from 3 to 35 mols per mol of organic compound to be dehydrogenated and excellent results have been obtained within the range of about 5 to about 30 mols of steam per mol of organic hydrocarbon to be dehydrogenated. The functions of the steam are several-fold and the steam may not merely act as a diluent. Diluents generally may be used in the same quantities as specified for the steam. These gases serve also to reduce the partial pressure of the organic compound.

The temperature for the dehydrogenation reaction generally will be at least about 250° C. such as between 300° C. or 375° C. and about 700° C. or 800° C. with the maximum temperature in the reactor of 900° C. under certain circumstances. Excellent results are obtained within the range of about 350° C. to 700° C., such as from about 400° C. to about 657° C.

The gaseous reactants may be conducted through the reaction chamber at a fairly wide range of flow rates. The optimum flow rates will be dependent upon such variables as the temperature reaction, pressure, particle size, and so forth. Desirable flow rates may be established by one skilled in the art. Generally, the flow rates will be within the range of about 0.1 to 10 liquid volumes of the organic compound to be dehydrogenated per volume of dehydrogenation zone containing catalyst per hour (referred to LHSV). Usually, the LHSV will be between 0.15 and about 5. For calculation, the volume of the fixed bed dehydrogenation zone containing catalyst is that original void volume of reactor space containing catalyst.

The zinc ferrites may be prepared by reacting an active compound of iron with an active compound of zinc. The term "active compound" is used here to mean a compound which is reactive under the conditions to form the ferrite. Starting material of iron and zinc may be nitrates, hydroxides, hydrates, oxalates, carbonates, acetates, formates, halides, oxides, and the like. Frequently, the active compounds are oxides or materials with decompose to oxides during the formation of the ferrite. The active compounds are intimately mixed by any of the conventional methods such as dry mixing, slurrying, coprecipatation or the like. The active compounds are reacted to form the ferrite by heating at an elevated temperature.

The temperature used for calcination may be varied, depending somewhat upon the type of atmosphere utilized. Speaking generally, higher temperatures may be employed to prepare the zinc ferrite compositions if a relatively non-oxidizing atmosphere is employed. For example, higher temperatures might be tolerated using nitrogen rather than air as the calcination atmosphere. At any rate, superior compositions are produced at calcination temperatures of from that high enough to form the ferrite to 1300° C. or less. Preferably, the ferrites are formed at a calcination temperature of from 400°–1100° C. in a controlled atmosphere such as mentioned hereinbefore. The calcination time at the elevated temperature may vary from five minutes to four or more hours.

The zinc ferrite having the formula $ZnFe_2O_4$ is formed during the calcination step. Preferably, the calcination occurs in an atmosphere containing less oxygen than normally contained in air, such as less than 15 or 20 mol percent oxygen. By thus causing the reaction to take place in an atmosphere deficient in oxygen, the zinc is less prone to be oxidized to a higher valence. The calcination to form the ferrite may be conducted essentially in the absence of air such as in an atmosphere of nitrogen or helium. In a preferred embodiment of the present invention, the ferrite catalyst material contains an excess of iron over the stoichiometric amount to form the ferrite. For the zinc ferrite of the present invention, the stoichiometric amount of iron is 2 atoms per atom of zinc. The iron (calculated as $Fe_2O_3$) may be present in an amount of at least about 10 percent in excess of the stoichiometric amount and preferably present in an amount of at least 14 percent excess of the stoichiometric amount. Suitable ranges of iron are from about 10 to 200 percent excess of the stoichiometric amount.

The ferrite formation may be conducted in the presence of catalysts to promote the ferrite formation. Halogens such as chlorine, bromine, and iodine and compounds thereof may be used. The preferred halogen is chlorine. Examples of catalysts used to promote ferrite formation are HCl, $Cl_2$, $Br_2$, zinc chloride, iron chloride, and the like.

A preferred manner of preparing the zinc ferrite catalyst composition is slurrying $ZnCO_3$ with $\alpha$-$Fe_2O_3$ and a halide in water and mixing the slurry for a sufficient time to obtain a homogeneous mixture. The mixture is then dried and the dried cake granulated and calcined at an elevated temperature. The calcined ferrite material is wetted with water and pelletized into pellets which are then dried.

A halide component of the slurry can be any suitable compound whereby the halogen will be available and in intimate contact with the other components during the calcination step. A preferred method is to introduce the halide by way of a solid inorganic compound which at least partially decomposes during the calcination step.

Metal or metalloid halides are satisfactory inorganic metal compounds. Iron or zinc halide (or hydrates thereof) are especially satisfactory as the iron and zinc are components of the resulting catalyst. Generally, the halogen will be chlorine, bromine or iodine with the chlorine being preferred.

The halide component of the slurry may be present in an amount of from about 0.5 to 10 mol percent of the total halide and zinc carbonate present in the slurry. Preferably, the halide will be present in an amount of from 1 to 5 mol percent based on the total zinc containing compounds in the slurry.

The catalyst compositions of the present invention may also comprise additives such as phosphorus, silicon or mixtures thereof. Excellent results are obtained with phosphorus and/or silicon present in an amount of from 0.2 to 20 weight percent based on the total weight of the catalyst composition. The catalyst compositions may also contain less than 5 weight percent and preferably less than 2 weight percent of sodium or potassium in the surface of the catalyst. The silicon, phosphorus, or other additives may be added at various stages in the preparation of the catalyst composition. Silica can be incorporated into the catalyst composition by the acid hydrolysis of an organic or inorganic silicate such as tetraethylortho silicate, for example. Another method of preparation incorporating silicate into the catalyst composition is to mix the silicate directly to the aqueous slurry whereby the silicate hydrolizes in the presence of the other components of the slurry. Similarly, if phosphorus is included in the catalyst composition, the phosphorus may be added in a variety of ways. One method is to mix the dried ingredients after calcination with the phosphorus compound. Alternatively, the phosphorus compound can be added directly to the aqueous slurry prior to drying and calcination. Various phosphorous or silicon compounds may be employed such as any of the phosphoric acids, phosphorus pentoxide, ethyl phosphate, amine phosphate, ammonium phosphate, phosphorus halides, phosphorus oxyhalides, silicon halides and so forth. The catalyst compositions of the present invention may also comprise minor amounts of other metals either as a diluent or as an additive so long as the novel characteristics of this invention are not destroyed. Any other metal should be present in a lesser weight percent as compared to either zinc or iron. For example, if the halide component is say chromium halide, the catalyst obtained after calcination will contain an amount of chromium corresponding to the amount of chromium contained in the chromium halide component.

As mentioned hereinbefore, the calcined catalyst material can be wetted and formed into homogeneous pellets. In addition, the calcined catalyst composition can be deposited on carriers or supports such as alumina, pumice, silica and so forth. Diluents and binders may also be used. When supported on a carrier or support, the catalyst composition will suitably be fine grained and the particle size of the catalyst composition should be less than 1000 microns.

The homogeneous pellets of catalyst composition or supported catalyst compositions may be in a form of having a high surface to volume ratio. Superior catalyst have been obtained from catalysts having a surface to volume ratio of at least 480 or 500 square feet of peripheral surface per cubic volume of catalyst. Preferably, the surface to volume ratio would be at least 600 ft.$^2$/ft.$^3$ and a preferred range is about 500 or 550 to about 750 ft.$^2$/ft.$^3$. High surface to volume catalysts can be obtained by various means such as grinding larger catalyst particles or by extrusion of paste or other compositions through small orfices. When catalyst are extruded through orifices, the orfice should be less than 3/32" in diameter with a preferred size orfice being about 1/16" in diameter or less. For example, the orfice could be from 2/64" to 5/64" in diameter. The average length of the particle will depend upon the particular composition being extruded and will vary e.g. from 1/16" to ¼" or longer. The term "surface" in the surface to volume ratio refers to the calculated peripheral surface assuming the surface is smooth rather than to the total surface including surface within the particle. The volume referred to is the volume of reactor space occupied by catalyst. For example, for cylindrical pellets, the number of catalyst particles in a unit volume of reactor space is determined and the average size of pellet is determined by measuring the pellets. The average peripheral surface of each pellet is calculated based on a cylinder of the average size pellet and the total calculated surface of the cylinders in the unit volume is determined to arrive at the square feet of surface per unit volume of reactor (ft.$^2$/ft.$^3$). The catalyst particles may be any shape such as cylindrical, spherical, irregular or any other shape of catalyst with these shapes being known to those skilled in the art. If the catalysts are spherical, the calculation of the catalyst surface to reactor volume will be done in similar manner to that described for the cylindrical pellets. When irregular shaped particles are employed, the peripheral catalyst surface may be determined by any of the analytical techniques for determining this type of surface such as disclosed in Canadian Journal or Chemical Engineering, Vol. 39, p. 49, Feb., 1961.

The catalysts are employed in fixed beds through which the reactants, diluents and the like previously described are passed. In addition to passing the gaseous materials through the fixed catalyst bed, some materials may be sparged into the bed, or into inert or void zones within the catalyst beds, such as, oxygen sparging into the reactant stream at points along the bed. Similarly, hydrocarbon feed or steam may be added in this manner.

The use of only steam for activation of zinc ferrite oxidative dehydrogenation catalysts improves the effective of the catalyst in the oxidative dehydrogenations and provides a simpler, more economic activation process than previously available in the art.

In the following examples will be found specific embodiments of the invention and details employed in the practice of the invention. Percent conversion refers to the mols of organic compound to be dehydrogenated that is consumed, based on the mols of the said organic compound fed to the reactor, percent selectivity refers to the mols of product formed based on the mols of the organic compound consumed, and percent yield refers to the mols of product formed based on the mols of the organic compound fed. All other percentages are by weight unless expressed otherwise. The presence of $ZnFe_2O_4$ was established by X-ray analysis as fully described in U.S. Pat. No. 3,420,911. The product analysis was by gas-liquid chromatography.

EXAMPLE 1

CATALYST PREPARATION

The following reagents were used:

| | | |
|---|---|---|
| ZnCl$_2$ | 61.8 | grams |
| α-Fe$_2$O$_3$ | 8603 | grams |
| ZnCO$_3$ | 3733.2 | grams |

The above reagents were added to demineralized water in a blender, and the mixture was slurried for 5 hours. The slurry was then dried for 12 hours in an oven at 260° F. to remove the water therefrom. The dried cake obtained upon the removal of the water from the slurry was granulated and dried at 260° F. for an additional 12 hours and calcined by passing through a rotary kiln at 1150° F. in air. The residence in the rotary kiln was approximately 14 minutes. The calcined material was then quenched to room temperature and 21 grams (1.5 wt.%) ZnCO$_3$ added to 1340 grams of the calcined material which was treated with a solution containing 190 cc of polyvinyl alcohol and 7 weight percent phosphoric acid. The damp mixture was then pelletized to 1/16 inch pellets which were dried in an oven at 250° F.

EXAMPLES 2-5

CATALYST EVALUATION

In these examples, the catalyst from Example 1 was employed in oxidative dehydrogenation by activating portions of the catalyst in different ways. In Example 2, there is no preheating or reduction of a fresh catalyst; in Example 3, the catalyst from Example 1 was preheated under steam. In Example 4 and 5, fresh samples of catalyst were preheated under steam. The feed was the same for each example and consisted primarily of normal butenes. Selectivity (S) and Yield (Y) are for butadiene-1,3(Y=SXC). The conditions of the activation and the oxidative dehydrogenation are set out below in the TABLE (LHSV 1.5 for activation and dehydrogenation).

| Example No. | Activation Conditions | O$_2$/Stm/HC | Tot. Hrs. on stream | C/S/Y | T$_i$ (° F.) | T$_{max}$ (° F.) |
|---|---|---|---|---|---|---|
| 2 | No Reduction No Preheating | 0.55/20/1 | 16¼ | 48.4/97.5/47.2 | 644 | 870 |
| 3 | Preheated for 3 hrs. at 850° F. under 15 mols steam (spent catalyst Ex. 2) | 0.55/17/1 | 16½ | 48.6/97.3/47.3 | 677 | 929 |
| 4 | Preheated for 3 hrs at 850° F. under 15 mols steam small trickle of N$_2$ | 0.55/20/1 0.55/18/1 0.55/17/1 | 65¼ 67¼ 222 | 65.6/96.2/63.1 71.6/96.9/68.7 67.6/95.4/64.5 | 640 640 645 | 890 925 925 |
| 5 | 3 hrs. at 850° F. under 15 mols steam 650 cc H$_2$/mm | 0.55/20/1 0.65/12/1 0.75/12/1 | 225½ 572 596 | 69.8/94.7/66.1 71.9/93.6/67.3 74.4/91.0/67.7 | 618 660 650 | 870 960 1055 |

Definitions of Abreviations:
Stm = steam
HC = total hydrocarbon in feed
O$_2$Stm/HC = mol ratio
C = conversion
S = selectivity
Y = yield
T$_i$ = inlet temperature
T$_{max}$ = maximum temperature in the catalyst bed at the time of sampling The activations with and without hydrogen are quite comparable, thus indicating that special facilities for producing hydrogen would not be required to produce a commercially acceptable degree of activation. The trickle of N$_2$ in Example 4 was to maintain the flow of steam through the laboratory equipment employed in these runs.

The reactor used consists of two 23-½ inch electric combustion furnaces mounted vertically one over the other about three inches apart. Each unit is capable of independent temperature control. Each of the two furnaces houses a 24×1 inch I.D., 316 stainless steel tube. These two tubes are joined by a common connection located between the two furnaces. The top tube contains an inert packing, e.g., 6×6 mm Vycor* raschig rings and is used to vaporize, mix and preheat reactants and/or diluents before they pass downflow over the catalyst bed contained in the bottom tube of the reactor system. The bottom tube contains 125 cc of catalyst. Vycor raschig rings (6×6 mm) are used to support the catalyst as a desired level in the tube and also to fill any void space remaining in the tube above the level of the top of the catalyst bed. The temperature of the catalyst bed is measured with thermocouples inserted into a ¼ inch, 316 ss thermowell located inside and coaxial with the reaction tube.

*Vycor is the trademark of Corning Glass and is comprised approximately of 96 percent silica with the remainder being essentially B$_2$O$_3$.

The invention claimed is:

1. A process for the oxidative dehydrogenation of organic compounds containing 2 to 20 carbon atoms and at least one

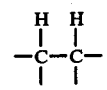

grouping comprising
depositing a particulate mass comprising zinc ferrite catalyst in a fixed bed,
intimately contacting said zinc ferrite with a continuous stream consisting of steam having a temperature of 700° to 1300° F., for a period of time to activate said zinc ferrite,
intimately contacting said activated zinc ferrite with said organic compounds in the presence of about 0.2 to 5 mols of oxygen per mol of said organic compound, 2 to 40 mols of steam per mol of said organic compound at a temperature at least about 250° C., and
recovering a product comprising more highly unsaturated organic compounds.

2. The process according to claim 1 wherein the temperature of the steam is in the range of 800° to 1200° F.

3. The process according to claim 2 wherein said organic compounds are hydrocarbons having 4 to 8 carbon atoms.

4. The process according to claim 3 wherein said hydrocarbons have 4 carbon atoms.

5. The process according to claim 1 wherein said contacting of activated zinc ferrite and organic compounds is at a temperature in the range of 300° to 700° C.

* * * * *